United States Patent
Dalgaard et al.

(10) Patent No.: US 7,130,429 B1
(45) Date of Patent: Oct. 31, 2006

(54) METHOD AND AN APPARATUS FOR PROCESSING AUSCULTATION SIGNALS

(75) Inventors: Torben Naurbo Dalgaard, Struer (DK); Lars Arknaes-Pedersen, Struer (DK)

(73) Assignee: Bang & Olufsen Technology A/S, Struer (DK)

( * ) Notice: Subject to any disclaimer, the term of this patent is extended or adjusted under 35 U.S.C. 154(b) by 0 days.

(21) Appl. No.: 09/283,587

(22) Filed: Apr. 1, 1999

(30) Foreign Application Priority Data

Apr. 8, 1998 (DK) .................................. 0517/98

(51) Int. Cl.
*A61B 7/04* (2006.01)
*A61F 11/06* (2006.01)

(52) U.S. Cl. ...................... 381/67; 381/71.6
(58) Field of Classification Search ............... 381/67, 381/71.6; 600/528
See application file for complete search history.

(56) References Cited

U.S. PATENT DOCUMENTS

| | | | |
|---|---|---|---|
| 4,220,160 A * | 9/1980 | Kimball et al. | ............. 600/528 |
| 4,436,096 A | 3/1984 | Dyck et al. | |
| 4,454,609 A * | 6/1984 | Kates | ......................... 381/320 |
| 4,905,706 A | 3/1990 | Duff et al. | |
| 4,972,841 A | 11/1990 | Iguchi | |
| 5,317,273 A * | 5/1994 | Hanson et al. | ............... 324/616 |
| 5,539,831 A * | 7/1996 | Harley | ......................... 381/67 |
| 5,557,681 A | 9/1996 | Thomasson | |

FOREIGN PATENT DOCUMENTS

| | | |
|---|---|---|
| EP | 0 596 785 A1 | 5/1994 |
| WO | WO 92/20284 | 11/1992 |
| WO | WO 97/00045 | 1/1997 |
| WO | WO 97/19640 | 6/1997 |

\* cited by examiner

*Primary Examiner*—Laura A. Grier
(74) *Attorney, Agent, or Firm*—David S. Safran (57) ABSTRACT

An apparatus for processing auscultation signals, e.g. embedded in an electronic stethoscope with a digital readout of an estimated heart rate. The apparatus comprises a bias processor for receiving an auscultation signal and providing a biased auscultation signal; said bias processor comprising an envelope detector and an estimator for calculating a signal representative of the beat frequency of the auscultation signal. In one aspect the information in the biased auscultation signal that is in conformity with the repeated information in the auscultation signal is enhanced. This may e.g. be done by calculating the conformity between the biased auscultation and at least a part of the biased auscultation signal. In another aspect of the invention the auscultation signal is biased by means of A-weighing. Preferably the two aspects of the invention are combined.

25 Claims, 7 Drawing Sheets

METHOD AND AN APPARATUS FOR PROCESSING AUSCULTATION SIGNALS

BACKGROUND OF THE INVENTION

1. Field of the Invention

This invention relates to a method of processing auscultation signals, consisting of the steps of receiving an auscultation signal and providing a biased auscultation signal, and calculating a signal representative of an estimated rhythm of the auscultation signal.

Moreover, the present invention relates to an apparatus for processing auscultation signals, and in particular to an electronic stethoscope suitable for use in cardiology.

2. Description of Related Art

In recent years physicians have had an impressive arsenal of instrumentation at their disposal for the diagnosis of cardiovascular diseases. One such instrument is the well known stethoscope used to detect sounds originating from the heart and adjacent large vessels. With the introduction of the stethoscope, auscultation grew into an art providing the clinician with valuable information of the functional integrity of the heart. Nowadays it is possible to process the information residing in the auscultation signal electronically by use of embedded knowledge obtained by clinical research. Therefore it is possible to relieve the clinician from trivial tasks. One such task may be to estimate the heart rate of a beating heart based on the auscultation signal.

The auscultation signal consists of characteristic sounds that originate from the contraction and expansion of the heart in the process of pumping blood, i.e. sounds caused by vibrations from acceleration and deceleration of blood. When a beating heart is auscultated it is not the beat frequency that is heard, but rather the characteristic sounds. Further, for mid-aged healthy persons in normal conditions, the characteristic sounds often denoted S1 and S2 related to a contraction and expansion of the heart, respectively, are separated in time by a sufficiently large interval that allows for perception of the characteristic sounds as individual sounds, i.e. the characteristic sounds, are typically separated by more than 150–200 milliseconds for adults and about 50 milliseconds for children. Typically, the characteristic sounds have a continuous frequency spectrum distributed between approximately 15 Hz and 100 Hz and peaking at 30–40 Hz.

However, the characteristic sounds may be superimposed with sounds originating from different types of vibrations in the heart. These sounds are the so-called murmurs, that may be caused by mechanisms such as blood turbulence or flutter of structures. Murmurs may be divided into two primary groups: a first group consists of random 'noisy' sounds and a second group consists of 'musical' sounds with a continuous narrow-band frequency spectrum. Experience has shown that in a human being the 'musical' sounds are typically related to the heart beat frequency. The frequency spectrum of murmurs may be distributed up to 500–2000 Hz.

The characteristic sounds may also be disturbed by spurious contractions of the heart appearing at certain or random points in time. Further, the characteristic sounds may also appear at random points in time. This phenomenon is known as arrhythmia.

When the sound of a beating heart including murmurs, if any, is auscultated by means of a transducer placed on e.g. the chest of a patient, then low-frequent rumble noise will be picked up by the transducer. This rumble noise may have a frequency content primarily distributed from just below the frequency of the heart rate towards DC.

In severe cases these disturbances are able to destroy the characteristic sounds in the auscultation signal completely or at least disturb the auscultation signal to such a degree that it may be impossible to estimate even an approximated heart rate by use of the prior art technology.

However, for a trained person using a non-electronic stethoscope, the information in the form of characteristic heart sounds is relatively easily recognisable from repetition to repetition and therefore relatively easy to count. This is due to the fact that the human perception of the auscultation signal is very good at diminishing the disturbances or artefacts and pay attention to the features in the auscultation signal that provides information for estimating the heart rate.

U.S. Pat. No. 4,972,841 discloses an electronic stethoscope with a pulse rate display for displaying an estimated pulse rate. In the stethoscope a transducer converts so-called Korotkoff sounds into electrical signals. Korotkoff sounds are sounds created by vibrating walls of collapsed vessels as blood is just allowed to flow through the vessel. The electrical signals are amplified and fed to a counter in which the detected pulse rate per unit time is calculated and the result is displayed as a digital pulse rate.

However, this patent is not concerned with estimation of heart rates originating from humans where the measured sound may be very different from expected normal heart sounds. The patent does not disclose any means adapted to suppress artefacts that may be confused with or mixed up with the information in the auscultation signal relating to the heart rate.

U.S. Pat. No. 4,436,096 discloses a digital heart rate stethoscope. A transducer produces electrical signals representing the heart sound of a human patient and a filter is connected to receive the electrical signals. The filter is a narrow-band band-pass filter whose passband is centered on a characteristic heart sound frequency e.g. 33 Hz. The filter is thereby adapted to improve the signal-to-noise ratio and enables the transducer to be used over a patient's clothing. The filtered signal is converted into pulses which are counted in a counter and displayed as a digital heart rate indication.

Again, this patent is not concerned with estimation of heart rates originating from humans where the measured sound may be very different from the expected normal heart sounds. Neither does this patent disclose any means adapted to suppress artefacts that may be confused with or mixed up with the information in the auscultation signal relating to the heart rate.

International Application WO 97/00045 discloses a stethoscope for examining the characteristic of sound waves made by a beating heart. The stethoscope comprises means for establishing a threshold wave form beyond which cyclic reference complexes appear and are identified, and a time measurement device for measuring the time elapsed between similar moments on adjacent reference complexes as an indicator of rate of heart beat.

In this stethoscope the heart rate is estimated based on the assumption that there is substantially no noise between the heart sounds originating from contraction and expansion of the heart. The stethoscope is therefore not suited for use of estimating heart rates of persons suffering from heart murmur or arrhythmia.

Other apparatuses for estimating the heart rate use means for determining the envelope of the auscultation signal. The envelope is determined by taking the absolute value of the auscultation signal and band-pass filtering the absolute value signal.

SUMMARY OF THE INVENTION

Consequently, the prior art involves the problem that the heart rate is estimated erroneously when some degree of murmurs and/or arrhythmia is present in the auscultation signal.

Thus the primary object of the invention is to provide a more precise and robust heart rate estimation, estimating the heart rate that originates from a real and blood pumping contraction and expansion of the heart.

This is achieved, when the apparatus mentioned in the opening paragraph is characterized in that the estimator is adapted for selecting at least a part of the biased auscultation signal as first signal and calculating the conformity between the first signal and the biased auscultation signal.

Consequently, it is possible to suppress artefacts and random noise in the auscultation signal that may be confused or mixed up with the information relating to the heart rate. There is thereby obtained a signal in which the heart rate is very well defined.

In an expedient apparatus for processing auscultation signals, the estimator calculates a cross-correlation function. This cross-correlation function supplies a well-defined signal having large signal values at good conformity and small signal values at poor conformity.

When the part of the biased auscultation signal represents one of a succession of cycles of the biased auscultation signal, the part may represent a reference cycle that is found ideal in some aspects.

In another expedient apparatus for processing auscultation signals, the estimator calculates an auto-correlation function. The auto-correlation function is especially expedient when the heart rate is relatively stable over a given time interval.

The quality of the auscultation signal can be validated by verifying at least one of the following three items in a signal representing the conformity of the auscultation signal:
a) time differences between located extreme values must be within predetermined limits;
b) minimum and maximum time differences in proportion to the mean of the time differences must be within predetermined limits;
c) the magnitude of the result of the correlation at the extreme values location must be within predetermined limits.

Then a preferred quality level may be defined by means of the preferred limits that are related directly to the statistics of rhythm estimation.

The bias processor may comprise a filter for calculating an A-weighted version of the auscultation signal or an approximated A-weighted version of the auscultation signal. Simulations have shown that an A-weighted version of the auscultation signal comprises sufficient information to estimate the heart rate in a consistent way in a variety of situations.

When the A-weighted version of the auscultation signal is calculated by means of an approximation corresponding to a double differentiation of the auscultation signal in a predetermined frequency range, the filtering process requires a minimum of computational effort.

The bias processor may consists of an adaptive band-pass filter for filtering the signals provided by the envelope detector; the band-pass filter at least having an upper and a lower pass-band, respectively, to select from; the adaptive band-pass filter comprising a controller selecting the lower pass-band when a relatively large fraction of a signal input to the band-pass filter has a low frequency and selecting the upper pass-band when a relatively low fraction of a signal input to the band-pass filter has a low frequency. Thus, it is possible to estimate the rhythm in the auscultation signal over a relatively wide range of frequencies while it is avoided that the signal-to-noise ratio is ruined, i.e. it is possible preserve a relatively narrow pass-band of the band-pass filter.

The auscultation signal may consist of samples that arrive at a sample rate, and the apparatus may consist of a synchronous processor operating at a rate corresponding to the sample rate, and further consisting of an asynchronous processor operating at time intervals that are initiated by a request. Hereby, it is possible to acquire new samples of the auscultation signal in real time while a correlation function operating on prior sample values of the auscultation signal is calculated.

Alternatively, the object of the invention is achieved when the apparatus is characterized in that the bias processor consists of a filter having a frequency response corresponding to an A-weighing or an approximated A-weighing, at least for a frequency range of interest.

Consequently, it is possible to estimate the heart rate of a beating heart, based on the characteristic sounds of the beating heart and murmurs related to the heart rate. Thus, the heart rate may be estimated based on murmurs relating to the heart rate if the characteristic sounds do not provide sufficient information for estimating the heart rate. Further, low frequency rumble noise is diminished and the high frequency components are enhanced, thereby providing well defined information of the relative location of the characteristic sounds with respect to time. This well defined information is suitable for estimating the heart rate electronically.

When the auscultation signal is filtered with a filter having a frequency response corresponding to a double differentiation, the computational effort required to calculate the A-weighted version of the auscultation is reduced.

The frequency range of interest may span the frequency range below 2000 Hz. The characteristic heart sounds and murmurs related to the heart rate comprise frequency components located in this frequency range and provide sufficient information in this range for estimating the rhythm of a beating heart.

Moreover, the invention also relates to methods of estimating the rhythm in auscultation signals.

The invention will be explained more fully below in connection with a preferred embodiment and with reference to the drawing, in which:

DETAILED DESCRIPTION OF PREFERRED EMBODIMENTS

Figure 1:
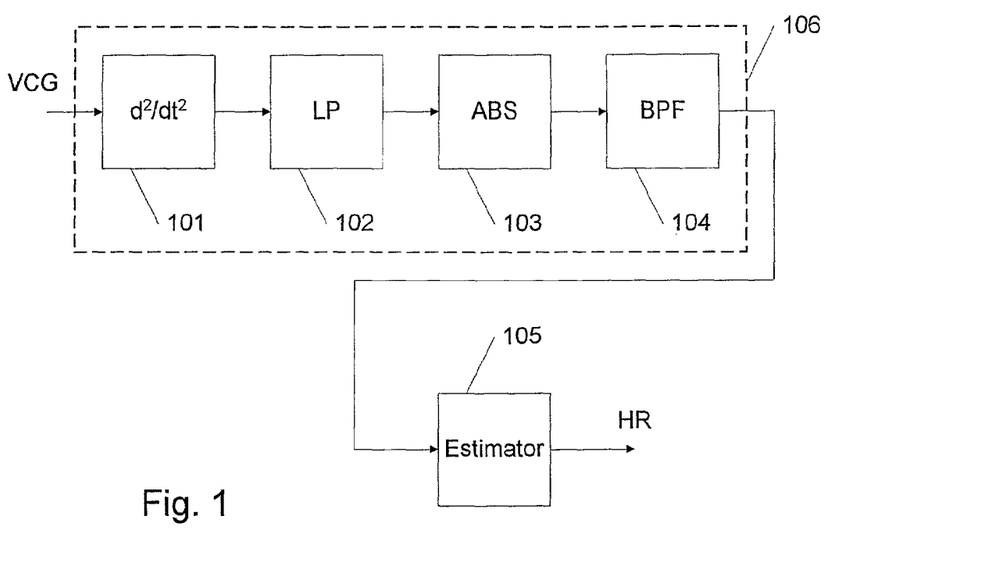
FIG. 1 shows a block diagram of a processor for processing auscultation signals by means of a bias filter calculating an approximated A-weighted auscultation signal.

FIG. 1 shows a block diagram of a processor for processing auscultation signals by means of a bias filter calculating an approximated A-weighted auscultation signal. An auscultation signal is a signal representing the acoustical signal that may be picked up by some type of transducer located to provide an auscultation signal representing the sound of a beating heart. The auscultation signal is hereinafter denoted VCG and may be a digital or analogue signal.

The block diagram comprises a bias processor 106. The VCG signal is filtered in the bias filter 101. The frequency response of the filter corresponds to an approximated A-weighing of the VCG signal. A-weighing is a linear model of the human ear modelling the human perception of signal amplitudes in the audio frequency range, i.e. about 20–20000 Hz. A-weighing is typically modelled as a second order band-pass filter with a centre frequency of 2000 Hz. The A-weighing model is approximated as a double differentiation of the VCG signal with respect to time thereby providing an A-weighted version, A-VCG, of the VCG signal. The approximation is valid for frequencies between about 20–200 Hz. The bias filter 101 may thus be viewed as a second order high-pass filter slope. The filter thereby diminishes low frequency rumble noise that may be present in the auscultation signal. Further, the filter enhances the upper part of the frequency spectrum of the characteristic heart sounds and eventually murmurs. However, the A-weighted signal A-VCG may also enhance noise originating from sources that are not related to either the characteristic heart sounds or eventually murmurs thereby destroying the signal-to-noise-ratio. The A-weighted signal A-VCG is therefore low-pass filtered by means of the filter 102. The low-pass filtered signal is then supplied as an input signal to the rectifier 102 that calculates the absolute value of the input signal and thereby provides an output signal. The output signal from the rectifier 103 is band-pass filtered in the filter 104. This band-pass filtered signal thereby constitutes the envelope of the A-weighted signal A-VCG. The band-pass filter has a pass-band corresponding to the range of expected heart rates e.g. from 0.5 to 3.3 HZ. Further, the stop-band of the band-pass filter diminishes any DC component and frequency components above the fundamental heart beat frequency, i.e. relative high frequency components.

The information in the band-pass filtered signal present as repetitive well-defined cycles is thereby representative of the heart rate. The heart rate may be estimated by means of an estimator 105. The estimator may be in the form of a peak locater determining the timing of the well-defined extreme values of the band-pass filtered signal. Alternatively, the estimator may be in the form of a threshold or zero-crossing detector thereby generating a square signal with a frequency representing the estimated heart rate. When the estimator comprises a threshold detector, the biased auscultation signal and a threshold value are both input to a comparator. The threshold value may be in the form of a constant value or an adaptive threshold value. The adaptive threshold value may be provided by a low-pass filter filtering the biased auscultation signal.

Figure 2:
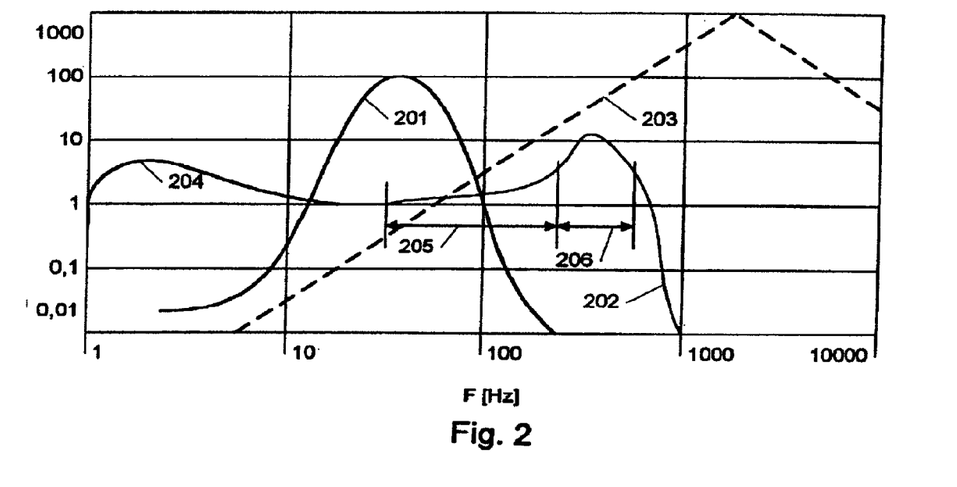
FIG. 2 shows the expected frequency spectrum of the characteristic heart sounds, a murmur, and rumble noise.

FIG. 2 shows the expected frequency spectrum of the characteristic heart sounds, a murmur, and rumble noise. The spectrums are rough approximations and for illustration purposes only. The magnitude Amp. of the spectrums are in arbitrary units and shown as a function of the frequency F. The frequency spectrum 201 of the characteristic heart sounds related to a contraction and an expansion of a beating heart is illustrated roughly. In the literature the sound related to a contraction is denoted S1 and the sound related to an expansion is denoted S2. The frequency spectrum of the frequency contents of S1 and S2 is primarily located between 20 and 50 Hz but may be distributed up to 100–200 Hz and down to below 10 Hz.

However, the frequency contents of murmurs are typically distributed at higher frequencies. This is shown by the frequency response 202. The frequency contents of murmurs comprising 'musical' sounds is distributed over a relatively narrow-band frequency range 206. This relative narrow band comprises information that may he used for estimation of the heart rate. Typically, murmurs are also associated with a relative broad band 205 not comprising information regarding the heart rate. An absolute numerical definition of these frequency bands and the magnitudes of the auscultation signal in these bands will depend on the murmur in question.

The frequency spectrum 204 of low-frequent rumble noise typically overlaps the frequency spectrum 201 of the characteristic heart sounds.

The transfer function 203 shows a preferred transfer function for a filter for calculating a biased auscultation signal. The filter is thereby able to enhance the amplitude of the frequency components of the upper part of the frequency spectrum of the characteristic heart sounds and the amplitude of the frequency components of the frequency spectrum of murmurs. Further, low-frequency rumble noise that may be present in the auscultation signal is diminished. The transfer function 203 consists of a high-pass 40 dB per decade slope. The slope may be a part of an approximated A-weighing function, where the approximation is implemented as a second order band-pass filter with a centre frequency of 2000 Hz.

Figure 3:
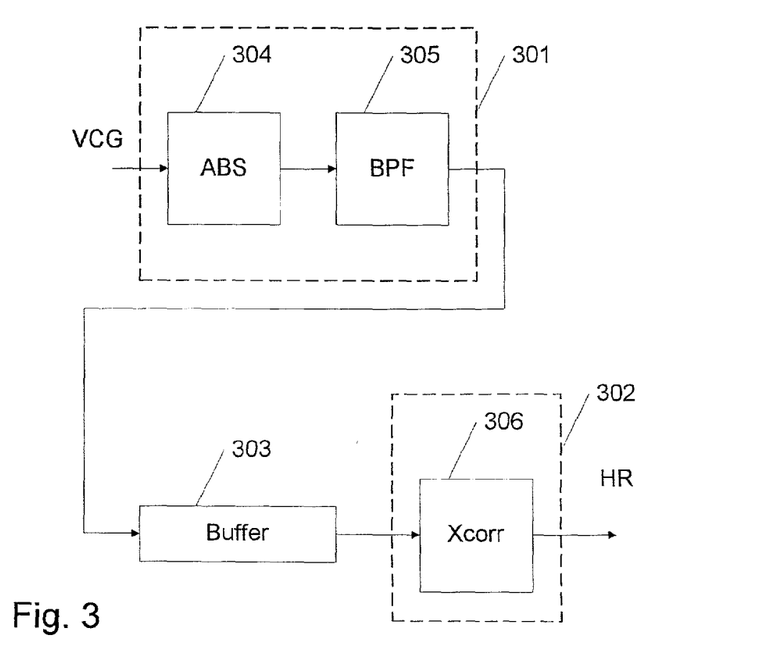
FIG. 3 shows a block diagram of a processor for calculating the beat frequency of an auscultation signal by means of a correlator.

FIG. 3 shows a block diagram of a processor for calculating the beat frequency of an auscultation signal by means of a correlator. In this embodiment the received auscultation signal VCG is a digital signal consisting of digital samples arriving at a sample frequency fs, e.g. fs equal to 4000 Hz.

The embodiment comprises a bias processor 301 processing the VCG samples at a rate synchronous with the sample frequency and an estimator 302 capable of operating asynchronously relative to the bias processor and providing a signal HR representative of the heart rate, when it is requested. The estimator 302 receives data in the form of samples from the bias processor 301 via the buffer 303. The buffer 303 may be in the form of a circular buffer or a first-in-first-out (FIFO) memory.

In the bias processor 301 the digital auscultation signal VCG is received and the respective absolute values of the VCG signal are calculated by means of the rectifier 304. Then the absolute values are band-pass filtered by means of the filter 305 in order to calculate the envelope of the auscultation signal. The band-pass filter has a passband corresponding to the range of expected heart rates e.g. from 0.5 to 3.3 HZ. Further, the stop-band of the band-pass filter diminishes any DC component and frequency components above the fundamental heart beat frequency, i.e. relatively high frequency components.

Samples from the band-pass filter are supplied to the buffer 303 at even points in time. The buffers may e.g. be circular buffers that have a capacity for a number of sample points, e.g corresponding to a signal sequence of 5 seconds. The oldest sample in the buffer is overwritten when a new sample arrives from the band-pass filter. Samples are taken from the buffer when the estimator 302 is initiated. The estimator may be initiated at certain regular or irregular points in time e.g. in order to provide information for the update of a digital display.

Although the envelope signal provided by the band-pass filter via the buffer 303 is smooth and comprises repetitive cycles it may be difficult to determine whether one or more cycles are present during a specific time interval. However, the information content in the envelope signal may be enhanced towards determining the exact number of cycles in a specific time interval. This is done by calculating the conformity of the envelope signal with respect to the envelope signal itself. This is based on the assumption that the vast majority of the cycles in the envelope signal represents an actual interrelated contraction and expansion of a heart in the process of pumping blood. The conformity of the envelope signal is calculated by means of the correlator 306 calculating the auto-correlation of the envelope signal.

In a preferred embodiment the correlator comprises means for selecting that cycle in the envelope signal that has the largest amplitude. This is done under the fair assumption that the largest amplitude in the auscultation signal is caused by a normal contraction/expansion of the heart that is least likely to comprise any artefacts. The extent of the selected cycle is found by searching for the nearest local minima that is less than zero. Thereby, falling into local minima with a magnitude greater than zero is avoided. This search for a minima is applied both forward and backward relative to the position of the largest amplitude. The selected cycle is stored and cross-correlated with the rest of the envelope signal. Alternatively, convolution or any other function capable calculating the conformity of a signal with respect to the signal itself may be used.

Figure 4:
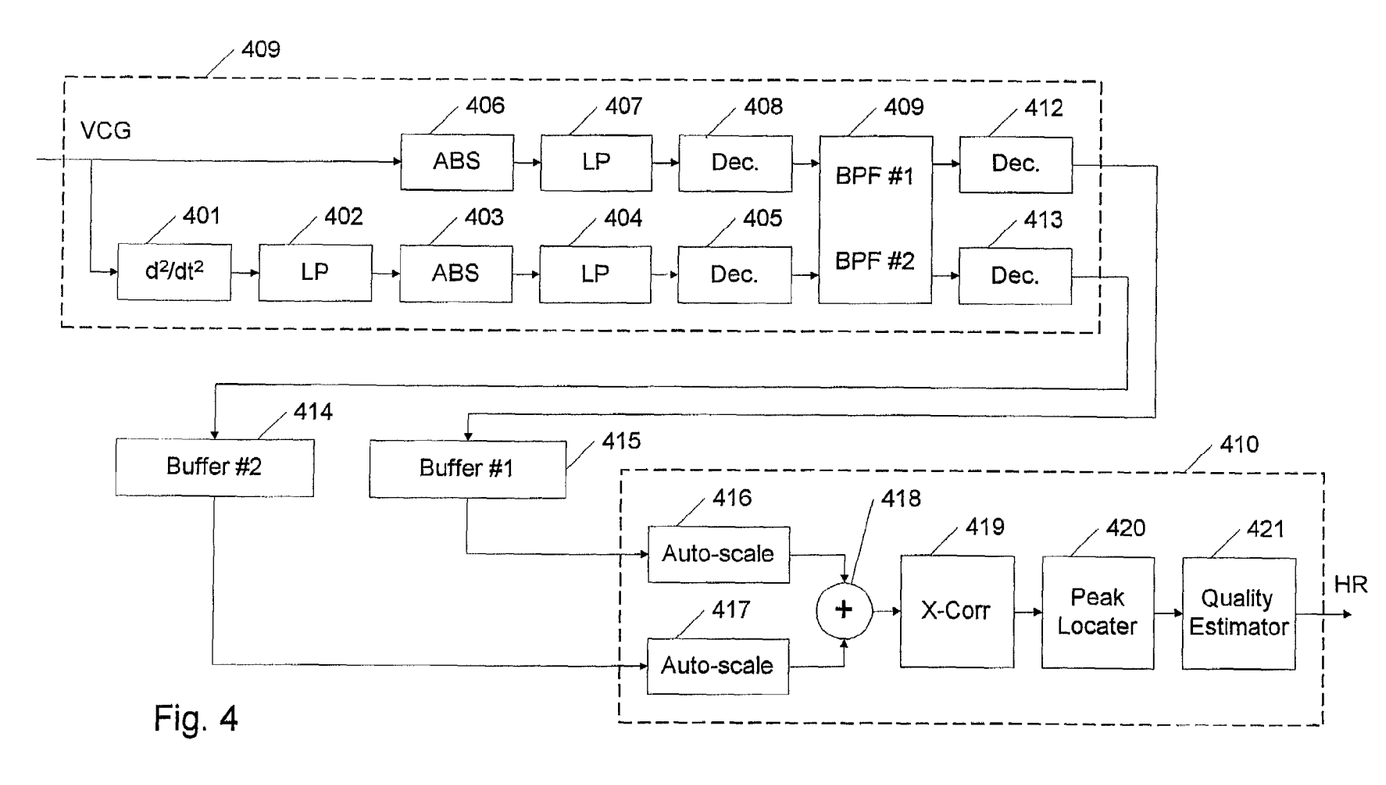
FIG. 4 shows a block diagram of a processor for calculating the beat frequency of an auscultation signal by means of a correlator and a bias filter comprising A-weighing.

FIG. 4 shows a block diagram of a processor for calculating the beat frequency of an auscultation signal by means of a correlator and a bias filter comprising A-weighing. In this preferred embodiment the bias filter comprising A-weighing and the correlator are combined in order to obtain an enhanced overall performance, i.e. it is possible to estimate the rhythm of a beating heart even though the characteristic sounds of the heart are distorted severely.

The auscultation signal VCG is in the form of a digital signal comprising sample values arriving at a sample frequency fs, e.g. fs=4000 Hz. The auscultation signal is branched. A first branch supplies the auscultation signal to a rectifier or an absolute value detector, ABS, 406. The absolute value of the auscultation signal is further supplied to the low-pass filter 407 having a cut-off frequency of about 3 Hz such that frequency components above 100 Hz is diminished. A second branch supplies the auscultation signal to the filter 401 in which the double derivative of the auscultation signal is calculated. The frequency response of the filter 401 corresponds to a second order high-pass slope or an A-weighing approximation in the frequency range below 2000 Hz. The double derivative of the auscultation signal is supplied to a low-pass filter 402 in which the relatively high frequency noise components enhanced by the differentiation in the filter 401 is damped. The filter 402 may have a cut-off frequency of about 100 Hz. The signal that is low-pass filtered by the filter 402 is supplied to a rectifier or an absolute value detector, ABS, 403. The absolute value of the auscultation signal is further supplied to the low-pass filter 407 that diminishes frequency components above 100 Hz.

The decimators, DEC, 405 and 408 generate a reduced sample rate $fs_R$, that e.g. may be 200 Hz since frequency components above 100 Hz is diminished. Thus, the computational effort required in the succeeding signal processing of the auscultation signal may be reduced.

The band-pass filter 411 comprising the band-pass filters BPF#1 and BPF#2 receives the decimated auscultation signals and calculates band-pass filtered signals. The band-pass filter may have a pass-band corresponding to the range of expected heart rates e.g. from 0.5 to 3.3 HZ. Note that DC components and frequency components above 25 Hz are diminished. The centre frequency of the band-pass filter may be adjusted adaptively in order to enhance the performance of the rhythm estimator. This is discussed later.

The band-pass filtered signals thus represent the envelopes of the auscultation signal and the double differentiated auscultation signal at a reduced sample rate.

The decimators, DEC, 412 and 413 generate a further reduced sample rate that may be e.g. 50 Hz since frequency components above 25 Hz are diminished. Thus, the computational effort required in the succeeding signal processing of the auscultation signal may be reduced even further.

Samples from the band-pass filter are supplied to the buffers 414 and 415 at even points in time. The buffers may e.g. be circular buffers that have a capacity for a number of sample points, e.g corresponding to a signal sequence of 5 seconds. Samples are taken from the buffers when the estimator 422 is initiated. The estimator may be initiated at certain regular or irregular points in time e.g. in order to provide information for the update of a digital display.

The samples that are taken from the buffers 414 and 415 are scaled by means of the auto-scale means 416 and 417 respectively. The auto-scale means may scale the received sample values by ensuring that the peak value over a number of scaled samples take the value 1.0, e.g. the number of samples may correspond to the signal sequence stored in the buffers 414 and 415, that is the signal sequence is normalised to a peak value equal to 1.0. The scaled samples are added in the adder 418 with equal weights since the information in the two signals are of equal importance, and the result of the addition is provided as a sum-signal. Alternatively, the two signals may be added with different weights.

The conformity of the sum-signal is calculated by means of the correlator, X-Corr, 419. In a preferred embodiment the correlator comprises means for selecting that cycle in the envelope signal that has the largest amplitude. The time extension of the selected cycle is found by searching for the nearest local minima that is less than zero. Thereby, falling into local minima with a magnitude greater than zero is avoided. This search for a minima is applied both forward and backward relative to the position of the largest amplitude. The selected cycle is stored and cross-correlated with the rest of the envelope signal.

The peak-locater 420 identifies extreme values in a signal representative of the result of the cross-correlation. This may e.g. be carried out by calculating the first derivative of the result of the cross-correlation and identifying inflexions. Preferably the peak-locater identifies maximums in the signal representative of the result of the cross-correlation.

The locations of the extreme values are preferably processed in a quality estimator 421. The estimator decides whether the result of the cross-correlation qualifies for estimating the rhythm, if any, of the auscultation signal. The quality estimator 421 may consist of three steps in the process of estimating the quality:
1. The mean of the time differences between two extreme values must be within predetermined limits;
2. The minimum and maximum time differences in proportion to the mean of the time differences must be within predetermined limits;
3. The magnitude of the result of the cross-correlation at the extreme values location must be within predetermined limits.

If one or more of the above mentioned items 1–3 fail, then it is determined that it is not possible to estimate any rhythm in the auscultation signal. Alternatively, if the above mentioned items pass, then it is possible to estimate a rhythm in the auscultation signal. The rhythm may be estimated by counting the number of extreme values in the result of the cross-correlation per time unit and displaying this as a number of beats per minute.

In alternative embodiments the correlators 306 or 419 can be adapted to calculate an auto-correlation function (i.e. two identical signals having a length corresponding to the capacity of the buffers 303 or 414, 415 are correlated with each other). A signal resulting from the calculation of the auto-correlation function can be used to estimate the rhythm of the auscultation signal and to examine the quality of the auscultation signals. A primary frequency of the auscultation signal is found by searching for a local maximum in the autocorrelation signal. The search is started from 0.3 seconds (200 bpm) and the primary frequency is defined as the first local maximum which exceeds a fixed threshold (if no local maximum is found before a 2 second limit in the autocorrelation, no primary frequency is determined). Before the primary frequency is approved, the following items has to be validated:
1. The mean level of the last 2 seconds of the buffer signal has to exceed a fixed threshold. This validation is done to prevent estimates based on the wrong kind of signals (or no signal at all).
2. There has to exist a peak in the autocorrelation located twice the time as the first peak (±approx 7.5%). This check is done to validate whether the buffer signal is periodic or not. This peak also has to exceed a fixed threshold.
3. If N peaks are found to the left of the first peak (peak1), the mean of the values found at the equally spaced locations=(peak1)/(N+1)→(N·peak1)/(N+1) has to be less than a fixed threshold. This check is done to prevent a low heart rate estimate if the envelope contains a component with a beat frequency equal to (N+1)·(primary frequency).
4. The estimate has to be stable over a time period. If the primary frequency is determined to be lower than 40 beats per minute (bmp), the estimate has to be stable (±30%) 8 times=1.6 second. If the main frequency is determined to be higher than or equal to 40 bmp, the estimate has to be stable (±30%) 4 times=0.8 second. This check is done to increase the validity of the estimate.

Other validation criteria may be feasible, but the above criteria has proved to work well.

Figure 5:
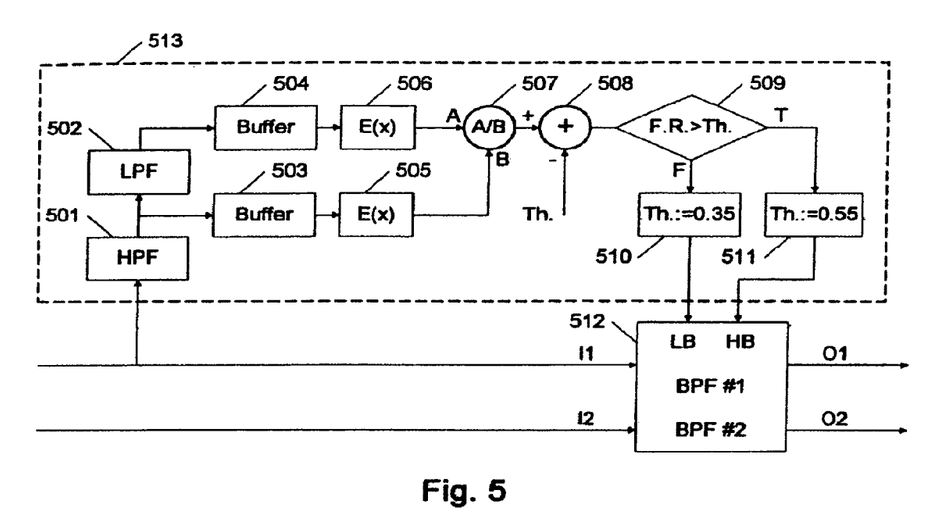
FIG. 5 shows an adaptive band-pass filter.

FIG. 5 shows an adaptive band-pass filter. This filter may be used instead of the band-pass filter 411 shown in FIG. 4. The adaptive filter may be used in estimation of the rhythm in the auscultation signal over a relatively wide range of frequencies while it is avoided that the signal-to-noise ratio is destroyed, i.e. it is possible preserve a relatively narrow pass-band of the band-pass filter.

The band-pass filter 512 receives two input signals I1 and I2 and provides two band-pass filtered output signals O1 and O2. The band-pass filter 512 thus comprises two band-pass filters BPF#1 and BPF#2. Each of the filters BPF#1 and BPF#2 comprises a pass-band LB with a relatively low centre frequency and a pass-band HB with a relatively high centre frequency. One of the pass-bands may be selected by supplying an enable signal to either the input LB or HB. This pass-band selection is carried out by the adaptive controller 513.

The high-pass filter 501 receives an input signal corresponding to one of the signals input to the band-pass filter 512. The high-pass filter 501 has a cut-off frequency of about 0.3 Hz thereby diminishing very low frequency components that is not used in the adaptive passband selection. The filter 501 supplies a high-pass filtered signal to the low-pass filter 502. The low-pass filter has a cut-off frequency of about 1 Hz.

The buffers 503 and 504 are capable of storing sample values corresponding to a signal sequence with a time duration of about 3 seconds, respectively. The expected or mean value of the sequences stored in the buffers are calculated by means of the mean value detectors 505 and 506. The mean value calculated by mean value detector 505 represents the mean value of the entire signal input to the band-pass filter 512. The mean value calculated by mean value detector 506 represents the mean value of the low-frequency part, i.e. below about 1 Hz, of the signal input to the band-pass filter 512.

Thus, the divider 507 calculates the fraction A/B of the signal that is relatively low-frequent. In an initial situation the threshold Th. is equal to the value 0.45. This value is subtracted from the fraction A/B by means of the adder 508. In the decision state 509 it is verified whether the frequency ratio A/B is greater than the threshold value. If this is the case (T) then the threshold value Th. is set equal to the value 0.35 and the pass-band LB having a relatively low centre frequency is selected. This is carried out under the assumption that the auscultation signal originates from a slow beating heart. Thus it is possible to diminish higher and superfluous frequency components by selecting the pass-band LB having a relatively low centre frequency. Preferably, the relatively low centre frequency is about 0.7 Hz.

Alternatively, if the frequency ratio A/B is less than the threshold value Th. (F), then the threshold value Th. is set equal to the value 0.55 and the pass-band HB having a relatively high centre frequency is selected. This is carried out under the assumption that due to the lack of low-frequency content in the auscultation signal, the auscultation is likely to originate from a very fast beating heart, e.g. from a child. By selecting the passband HB having a relatively high centre frequency there is maximum likelihood that the rhythm of the auscultation signal is estimated correctly. Preferably, the relatively high centre frequency is about 1.2 Hz.

Figure 6:
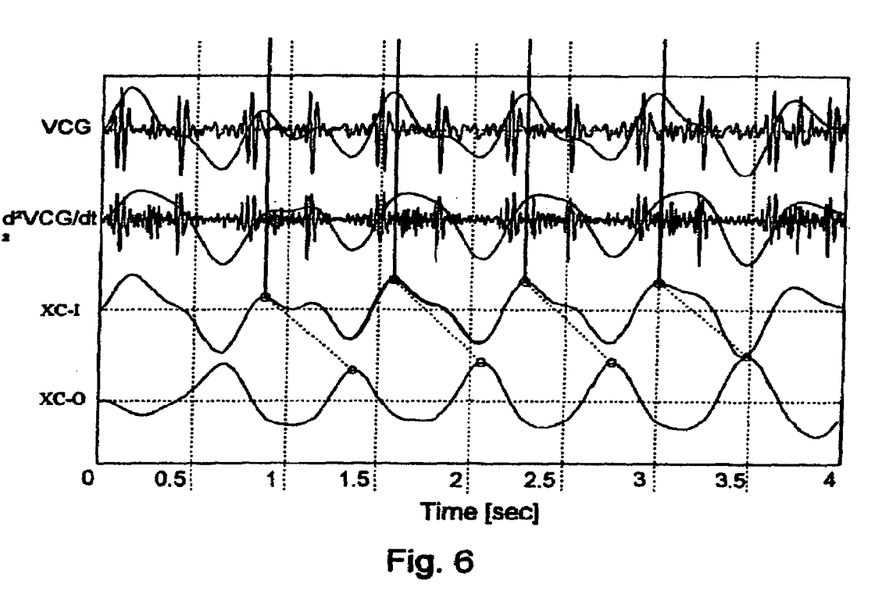
FIG. 6 shows signals related to an embodiment using a correlator and a bias filter comprising A-weighing.

FIG. 6 shows signals related to an embodiment using a correlator and a bias filter comprising A-weighing. The auscultation signal VCG and the corresponding band-pass filtered envelope of the VCG signal is shown as a function of time. Further, the A-weighted or double differentiated auscultation signal $d^2VCG/dt^2$ and the corresponding band-pass filtered envelope is shown. In view of a graphical interpretation it is clear that the heart rate could be estimated by using only one of the band-pass filtered signals. However, a stronger estimate is provided if the signals are added and used as input to a correlator as described above. This is shown by means of the signals 'XC-I' and 'XC-O'.

Figure 7:
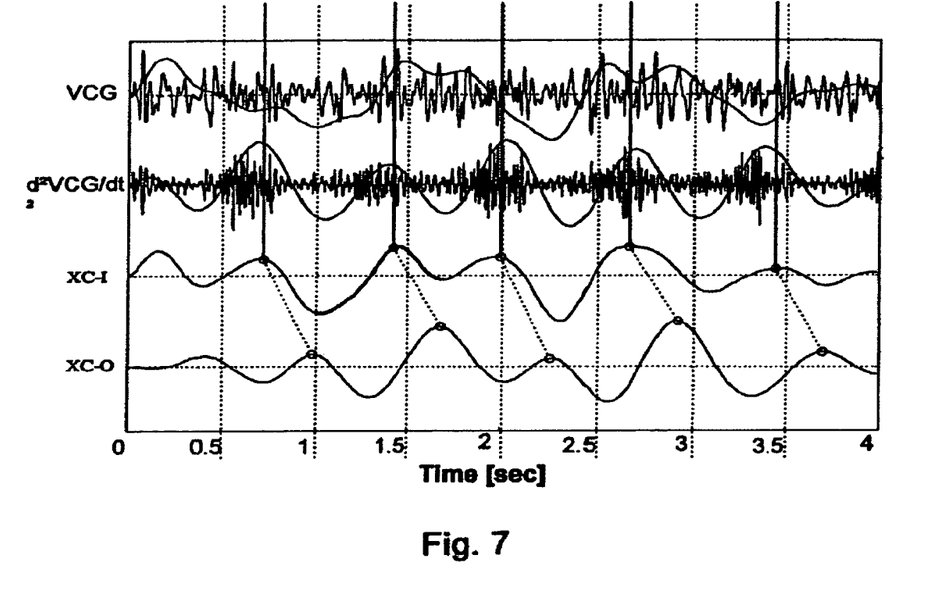
FIG. 7 shows an example of the information in the envelope of the auscultation signal being insufficient.

FIG. 7 shows an example of when the information in the envelope of the auscultation signal is insufficient. The auscultation signal VCG and the corresponding band-pass filtered envelope of the VCG signal is shown as a function of time. Further, the A-weighted or double differentiated auscultation signal $d^2VCG/dt^2$ and the corresponding band-pass filtered envelope is shown. In view of a graphical interpretation it is clear that the strongest estimate is provided by the double differentiated auscultation signal $d^2VCG/dt^2$. However, for the vast majority of auscultation signals the signal 'XC-O' provides the strongest overall estimate.

Figure 8:
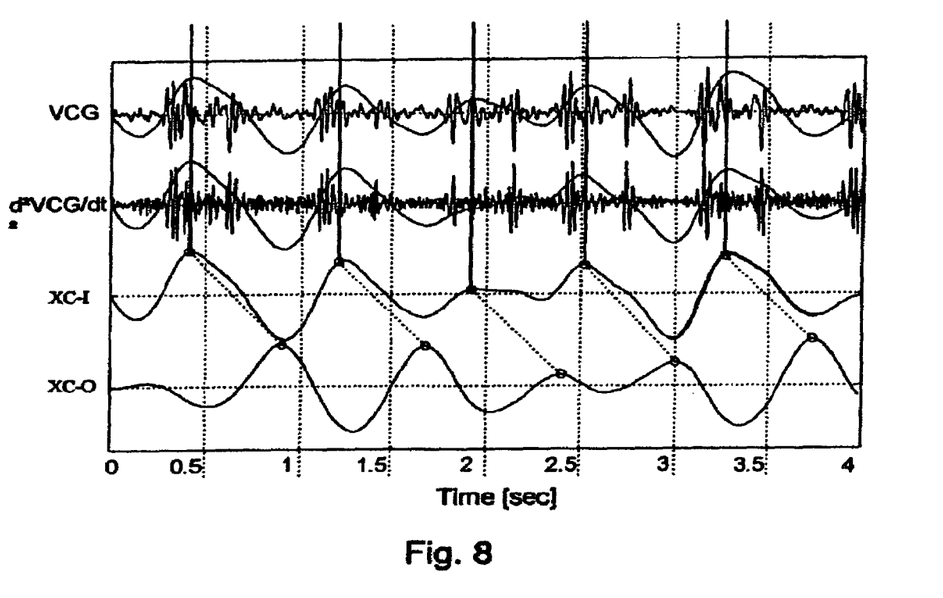
FIG. 8 shows an example of the information in the envelope of the A-weighted auscultation signal being insufficient.

FIG. 8 shows an example of when the information in the envelope of the A-weighted auscultation signal is insufficient. The auscultation signal VCG and the corresponding band-pass filtered envelope of the VCG signal is shown as a function of time. Further, the A-weighted or double differentiated auscultation signal $d^2VCG/dt^2$ and the corresponding band-pass filtered envelope is shown. In view of a graphical interpretation it is clear that the band-pass filtered VCG envelope signal provides the strongest estimate. But, again, the signal 'XC-O' provides the strongest overall estimate.

The invention may be embodied as a part of a stethoscope or any other instrument or apparatus. Alternatively, the invention may be embodied as a computer program or a part of a computer program, which may be loaded into the memory of a computer and executed therefrom. The computer program may be distributed by means of any data storage or data transmission medium. The storage media can be magnetic tape, optical disc, compact disc (CD or CD-ROM), mini-disc, hard disk, floppy disk, ferroelectric memory, electrically erasable programmable read only memory (EEPROM), flash memory, EPROM, read only memory (ROM), static random access memory (SRAM), dynamic random access memory (DRAM), ferromagnetic memory, optical storage, charge coupled devices, smart cards, etc. The transmission medium can be a network, e.g. a local area network (LAN), a wide area network (WAN), or any combination thereof, e.g. the Internet. The network may comprise wire and wire-less communication links. Via the network a software embodiment (i.e. a program) of the invention, or a part thereof, may be distributed by transferring a program via the network.

The invention claimed is:

1. An apparatus for processing auscultation signals, comprising:
   a bias processor that receives an auscultation signal from a single channel input and provides a biased auscultation signal representing the envelope of the auscultation signal received, said bias processor comprising an envelope detector; and
   an estimator that calculates a signal that represents an estimated rhythm of the auscultation signal received from the single channel input, the estimator selecting a part of the biased auscultation signal as a first signal, and calculating a conformity between the first signal and the biased auscultation signal.

2. The apparatus according claim 1, the estimator applying a cross-correlation function.

3. The apparatus according to claim 1, the first signal representing one of a succession of cycles of the biased auscultation signal.

4. The apparatus according to claim 1, the estimator applying an auto-correlation function.

5. The apparatus according to claim 1, a quality of the received auscultation signal being validated by verifying at least one of three items in a signal representing a conformity of the received auscultation signal, the three items comprising:
   a) time differences between located extreme values being within predetermined limits;
   b) minimum and maximum time differences in proportion to a mean of the time differences being within predetermined limits; and
   c) a magnitude of a correlation result at the extreme values location being within predetermined limits.

6. The apparatus according to claim 1, the bias processor comprising a filter that calculates one of an A-weighted version of the received auscultation signal, and an approximated A-weighted version of the received auscultation signal.

7. The apparatus according to claim 6, the A-weighted version of the auscultation signal being calculated by an approximation corresponding to a double differentiation of the received auscultation signal.

8. The apparatus according to claim 1, the bias processor comprising an adaptive band-pass filter that filters signals provided by the envelope detector, said adaptive band-pass filter having at least an upper pass-band and a lower pass-band, respectively selectable, and a controller that selects the lower pass-band when a relatively large function of a signal input to the adaptive band-pass filter has a low frequency and selects the upper pass-band when a relatively low fraction of a signal input to the band-pass filter has a low frequency.

9. The apparatus according to claim 1, the received auscultation signal comprising samples that arrive at a sample rate, the apparatus further comprising:
   a synchronous processor that operates at a rate corresponding to the sample rate; and
   an asynchronous processor that operates time intervals initiated by a request.

10. The apparatus according to claim 1, comprising a stethoscope that estimates a rhythm in the received auscultation signal.

11. An apparatus for estimating a rhythm in auscultation signals, comprising:
   a bias processor that receives an auscultation signal from a single channel input obtained from a single sensor and provides a biased auscultation signal, the bias processor comprising an envelope detector; and
   an estimator that calculates a signal representative of an estimated rhythm of the auscultation signal received from the single channel input, the bias processor comprising a filter having a frequency response corresponding to at least one of an A-weighing and an approximated A-weighing for a frequency range of interest.

12. The apparatus according to claims 11, the frequency range of interest being in a frequency range of less than 2000 Hz.

13. An apparatus for estimating a rhythm in auscultation signals, comprising:
   a bias processor that receives an auscultation signal from a single channel input and provides a biased auscultation signal, the bias processor comprising an envelope detector; and
   an estimator that calculates a signal representative of an estimated rhythm of the auscultation signal received from the single channel input, the bias processor comprising a filter having a frequency response corresponding to at least one of an A-weighing and an approximated A-weighting for a frequency range of interest, the auscultation signal being filtered with a filter having a frequency response corresponding to a double differentiation.

14. A method of processing auscultation signals, comprising:

receiving an auscultation signal from a single channel input; providing a biased auscultation signal;

calculating a signal representative of an estimated rhythm of the auscultation signal received from the single channel input;

the estimated rhythm being calculated by selecting a part of the biased auscultation signal as a first signal and calculating a conformity between the first signal and the biased auscultation signal.

15. The method according to claim 14, further comprising applying a cross-correlation function to calculate the representative signal.

16. The method according to claim 14, the selected part of the biased auscultation signal representing one of a succession of cycles of the biased auscultation signal.

17. The method according to claim 14, further comprising:
applying an auto-correlation function to calculate the representative signal.

18. The method according to claim 14, further comprising validating a quality of the received auscultation signal by verifying at least one of three items in a signal representing a conformity of the received auscultation signal, the three items comprising:
a) time differences between located extreme values being within predetermined limits;
b) minimum and maximum time differences in proportion to a mean of the time differences being within predetermined limits; and
c) a magnitude of the result of a correlation result at the extreme values location being within predetermined limits.

19. The method according to claim 14, further comprising:
calculating one of an A-weighted version of the received auscultation signal and an approximated A-weighted version of the received auscultation signal.

20. The method according to claim 14, the A-weighted version of the received auscultation signal being calculated using an approximation corresponding to a double differentiation of the received auscultation signal.

21. The method according to claim 14, further comprising:

filtering the biased auscultation signal using an adaptive band-pass filter, said adaptive band-pass filter having at least an upper pass-band and a lower pass-band respectively selectable, and being controlled such that the lower pass-band is selected when a relatively large fraction of a signal input to the adaptive band-pass filter has a low frequency and such that the upper pass-band is selected when a relatively low fraction of a signal input to the band-pass filter has a low frequency.

22. The method according to claim 14, the received auscultation signal comprising samples that arrive at a sample rate, the method further comprising:
executing synchronous steps at a rate corresponding to the sample rate, and executing asynchronous steps at time intervals initiated by a request.

23. The method according to claim 14, the frequency range of interest being in a frequency range of less than 2000 Hz.

24. A method for estimating a rhythm in auscultation signals, comprising:
receiving an auscultation signal from a single channel input obtained from a single sensor;
providing an biased auscultation signal; and
calculating a signal representative of an estimated rhythm of the received auscultation signal received from the single channel input, the signal representative of the estimated rhythm being calculated using a filter having a frequency response corresponding to at least one of an A-weighting and an approximated A-weighting for a frequency range of interest.

25. A method for estimating a rhythm in auscultation signals, comprising:
receiving an auscultation signal from a single channel input;
providing an biased auscultation signal; and
calculating a signal representative of an estimated rhythm of the received auscultation signal received from the single channel input, the signal representative of the estimated rhythm being calculated using a filter having a frequency response corresponding to at least one of an A-weighting and an approximated A-weighting for a frequency range of interest;
wherein the frequency response is obtained using a double differentiation.

* * * * *